(12) United States Patent
Lui et al.

(10) Patent No.: US 8,580,973 B2
(45) Date of Patent: Nov. 12, 2013

(54) PROCESS FOR THE PREPARATION OF 2,2-DIFLUOROETHYLAMINE

(75) Inventors: Norbert Lui, Odenthal (DE); Jens-Dietmar Heinrich, Burscheid (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 13/356,071

(22) Filed: Jan. 23, 2012

(65) Prior Publication Data

US 2012/0190867 A1    Jul. 26, 2012

Related U.S. Application Data

(60) Provisional application No. 61/435,497, filed on Jan. 24, 2011.

(30) Foreign Application Priority Data

Jan. 24, 2011   (EP) .................................. 11151873

(51) Int. Cl.
*C07D 207/408*    (2006.01)
(52) U.S. Cl.
USPC ....................................................... 548/545
(58) Field of Classification Search
USPC ....................................................... 548/545
See application file for complete search history.

(56) References Cited

U.S. PATENT DOCUMENTS

| 4,030,994 | A | * | 6/1977 | Kollonitsch | ............ | 204/157.79 |
| 2009/0253749 | A1 | * | 10/2009 | Jeschke et al. | ................ | 514/336 |
| 2010/0048646 | A1 | * | 2/2010 | Jeschke et al. | ................ | 514/357 |
| 2010/0274021 | A1 | | 10/2010 | Lui et al. | | |

FOREIGN PATENT DOCUMENTS

| HU | 9702472 | | 2/2000 | | |
| WO | WO2007115644 | * | 10/2007 | ............ | C07D 405/12 |
| WO | WO2008009360 | * | 1/2008 | ............ | C07D 213/57 |
| WO | 2009/036901 | | 3/2009 | | |

OTHER PUBLICATIONS

March (March's Advanced Organic Chemistry, 5th ed., (2001)).*
Cherbuliez et al. (Helv. Chimica Acta, 43 (1960), p. 1135-1142).*
Zhang et al. (Canadian Journal of Chemistry (1990), 68(10), 1668-75).*

International Search Report of PCT/EP2012/050834 Dated Feb. 15, 2012.
Swarts, "Ueber Einige Fluorhaltige Alkylamine," Chem Zentralblatt, vol. 75, pp. 944-945, (1904).
Dickey et al., "Fluorinated Aminoanthraquinone Dyes," Industrial and Engineering Chemistry, vol. 48, 2, pp. 209-213, (Feb. 1956).
Hudlicky, "Chemistry of Organic Fluorine Compounds," vol. 2, pp. 489-495, (1976).
Houben-Weyl, "B.Syntesis of Fluorinated Compounds," vol. E 10b/2, pp. 92-98, (2007).
Verniest et al., "Synthesis and Reactivity of 1-Substituted 2-Fluoro- and 2,2-Difluoroaziridines," J. Org. Chem. vol. 72, pp. 8569-8572, (2007).
Evans, "2-Fluoro-and 2,2-Difluoroethylnitroguanidine," J. Org. Chem., vol. 23, pp. 1077-1078, (1958).

* cited by examiner

*Primary Examiner* — Robert Havlin
(74) *Attorney, Agent, or Firm* — Miles & Stockbridge P.C.

(57) ABSTRACT

A process for the preparation of 2,2-difluoroethylamine, comprising the reaction of 2,2-difluoro-1-chloroethane with an imide of the formula (II)

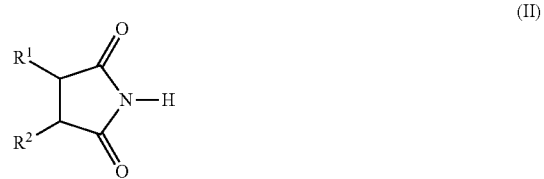

(II)

in the presence of an acid scavenger, to give a compound of the formula (III)

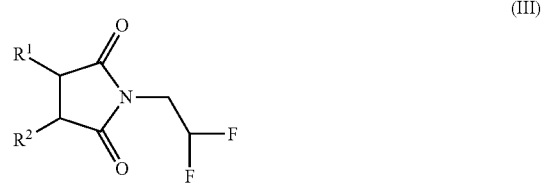

(III)

in which, in the compounds of the formulae (II) and (III), $R^1$ and $R^2$ are, each independently of one another, hydrogen or $C_1$-$C_6$-alkyl or $R^1$ and $R^2$ form, together with the carbon atoms to which they are bonded, a six-membered aromatic ring which is optionally substituted; and the cleavage of 2,2-difluoroethylamine by reaction of the compound of the formula (III) with acid, base or hydrazine.

1 Claim, No Drawings

PROCESS FOR THE PREPARATION OF 2,2-DIFLUOROETHYLAMINE

CROSS REFERENCE TO RELATED APPLICATIONS

This application claims priority to European Patent Application No. 11151873.4, filed Jan. 24, 2011 and U.S. Provisional Application No. 61/435,497 filed Jan. 24, 2011, the content of both of which are incorporated herein by reference in their entireties.

BACKGROUND

1. Field of the Invention

The present invention relates to a process for the preparation of 2,2-difluoroethylamine starting from 2,2-difluoro-1-chloroethane.

2. Description of Related Art

The compound 2,2-difluoroethylamine is an important intermediate in the preparation of active substances. Various methods for the preparation of 2,2-difluoroethylamine are known (e.g., Schwartz et al., Chem. Zentralblatt, Volume 75, 1904, pages 944-945; Dickey et al., Industrial and Engineering Chemistry, 1956, No. 2, 209-213). The known processes are disadvantageous since they either have a very long reaction time with only a low yield or because the reaction mixtures are highly corrosive, for which reason the known processes are unsuitable for commercial-scale use.

Starting from the known processes for the preparation of 2,2-difluoroethylamine, the question now arises of how 2,2-difluoroethylamine can be prepared in a simple and inexpensive way. The inventors have found that 2,2-difluoroethylamine can be prepared particularly advantageously if an imide intermediate is first prepared and then cleaved.

SUMMARY

A subject-matter of the invention is accordingly a process for the preparation of 2,2-difluoroethylamine comprising the following steps:

Step (i): Reaction of 2,2-difluoro-1-chloroethane of the formula (I)

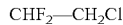

$$CHF_2-CH_2Cl \quad (I)$$

with an imide of the formula (II)

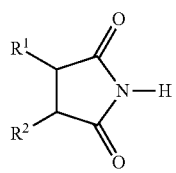

(II)

in the presence of an acid scavenger, in particular a base, to give a compound of the formula (III)

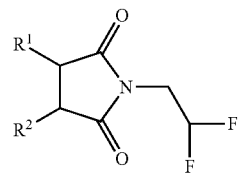

(III)

in which, in the compounds of the formulae (II) and (III), $R^1$ and $R^2$ are, each independently of one another, hydrogen or $C_1$-$C_6$-alkyl or $R^1$ and $R^2$ form, together with the carbon atoms to which they are bonded, a six-membered aromatic ring which is optionally substituted; preferably, the six-membered ring is optionally substituted with halogen or $C_1$-$C_{12}$-alkyl;

Step (ii): Cleavage of 2,2-difluoroethylamine by reaction of the compound of the formula (III) with acid, base or hydrazine.

DETAILED DESCRIPTION OF A PREFERRED EMBODIMENT

The imide of the formula (II) used in step (i) can also be present as salt. Such salts are in some cases commercially available (e.g., potassium salt of phthalamide). Before the salt is used in the process according to the invention, the imide of the formula (II) can also be converted to a salt by reaction with a suitable base. Suitable bases are known to a person skilled in the art or comprise the bases mentioned in the present case as acid scavenger.

It is preferable, in the process according to the invention, to use a compound of the formula (II) in which $R^1$ and $R^2$ are each hydrogen (i.e., succinimide) or in which $R^1$ and $R^2$ form, together with the carbon atoms to which they are bonded, a six-membered aromatic ring (i.e., phthalamide). If succinimide is used as compound of the formula (II), the compound of the formula (III-a) is obtained in step (i), which compound is novel. If phthalamide is used as compound of the formula (II), the compound of the formula (III-b) is obtained in step (i):

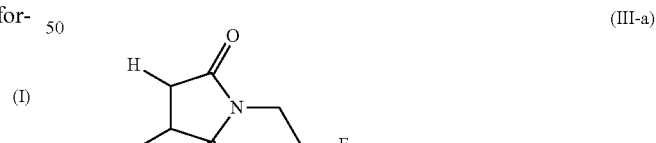

(III-a)

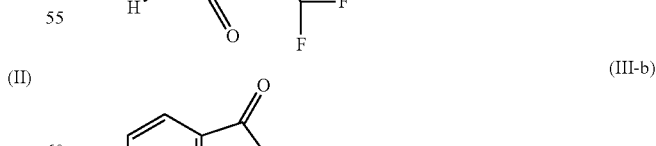

(III-b)

The process according to the invention can be illustrated by the following scheme:

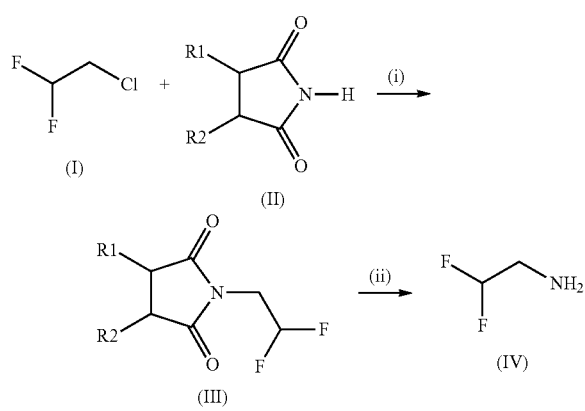

Although it is known, from Chemistry of Organofluorine Compounds (1976), 2$^{nd}$ edition, pp. 489-490, and Houben Weyl, E 10b/2, pp. 92-98, that a 2,2-difluoro-1-halothane compound reacts under basic conditions with elimination of HCl, HBr or HI to give vinylidene fluoride and is accordingly no longer available for the reaction in step (i), and although it is known, from J. Org. Chem., 2007, 72 (22), p. 8569, that 2,2-difluoroethylamine is very reactive and it is accordingly very probable that the imide of the formula (III) obtained will react further under the reaction conditions according to the invention of step (i), the inventors have found, surprisingly, that the imide of the formula (III) is obtained with a good yield and purity. An extensive purification can accordingly be dispensed with. At the end of the day, the target compound, 2,2-difluoroethylamine, is accordingly also obtained in a very good yield, based on the starting materials used in step (i).

It was likewise surprising that the 2,2-difluoro-1-chloroethane used in step (i) can be converted very well and with a yield of more than 90% to the imide of the formula (III). To be exact, it is known that chloroalkanes are not as reactive as bromo- or iodoalkanes and accordingly do not react very efficiently with imides, in particular substituted or unsubstituted phthalimides.

The use of 2,2-difluoro-1-bromoethane for the preparation of N-(2,2-difluoroethyl)phthalimide (corresponds to the compound of the formula (III-b)) is known and is described by Evans, R., Milani, V., Hather, L. S, and Skolnik, Sol. in Journal of Organic Chemistry (1958), 23, pp. 1077-1078. In the reaction described, 2,2-difluoro-1-bromoethane is reacted with potassium phthalimide in DMF at 210° C., N-(2,2-difluoroethyl)phthalimide being obtained in a yield of 47%.

The method described by Evans et al. for the preparation of N-(2,2-difluoroethyl)phthalimide is disadvantageous since, first, it has to be carried out at very high temperatures and, secondly, the yield is only 47%. The process likewise has an undesirable material balance since, in the reaction, approximately 50% of the mass of 2,2-difluoro-1-bromoethane used is lost because of the high molecular weight of bromine.

The term "material balance" is understood to mean, in general, the orderly comparison, according to type, of the amounts of material input and material output of a productive system. With a good material balance, the amount (mass) of the input corresponds to the amount (mass) of the output.

The use of 2,2-difluoro-1-chloroethane in the reaction according to the invention contributes to the reaction having a better material balance.

Compounds of the formula (II) are known, are commercially available or can be prepared according to normal methods.

Unless otherwise indicated, the expression "alkyl", in isolation or in combination with other terms, such as, e.g., mentioned in connection with the catalysts according to the invention, for example tetraalkylammonium bromides, tetraalkylammonium iodides or tetraalkylphosphonium halides, refers to linear or branched saturated hydrocarbon chains with up to 12 carbon atoms, i.e. $C_1$-$C_{12}$-alkyl, preferably with up to 6 carbon atoms, i.e. $C_1$-$C_6$-alkyl, very preferably with up to 4 carbon atoms, i.e. $C_1$-$C_4$-alkyl.

Examples of such alkyls are methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl and n-dodecyl. The alkyls can be substituted with suitable substituents, e.g. with halogen.

Unless otherwise indicated, the expression "aryl" or "six-membered aromatic ring" refers to a phenyl ring.

Unless otherwise indicated, "halogen" or "hal" is fluorine, chlorine, bromine or iodine.

The reaction of 2,2-difluoro-1-chloroethane of the formula (I) with an imide of the formula (II) in step (i) can be carried out neat, i.e. without adding a solvent, or in the presence of a solvent.

In the event that a solvent is added to the reaction mixture in step (i), it is preferably used in such an amount that the reaction mixture remains satisfactorily stirrable during the entire process. Use is advantageously made, based on the volume of the 2,2-difluoro-1-chloroethane used, of the solvent in an amount of 1 to 50 times, preferably in an amount of 2 to 40 times and particularly preferably in an amount of 2 to 20 times. The term "solvent" is also understood to mean, according to the invention, mixtures of pure solvents.

All organic solvents which are inert under the reaction conditions are suitable solvents. Suitable solvents according to the invention are in particular ethers (e.g., ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, 2-methyltetrahydrofuran, dioxane, and ethylene oxide and/or propylene oxide polyethers); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide or diisoamyl sulphoxide; sulphones, such as dimethyl, diethyl, dipropyl, dibutyl, diphenyl, dihexyl, methyl ethyl, ethyl propyl, ethyl isobutyl and tetramethylene sulphone; aliphatic, cycloaliphatic or aromatic hydrocarbons (e.g., pentane, hexane, heptane, octane, nonane, such as white spirits with components with boiling points in the range, for example, from 40° C. to 250° C., cymene, benzine fractions within a boiling point interval from 70° C. to 190° C., cyclohexane, methylcyclohexane, petroleum ether, ligroin, octane, benzene, toluene or xylene); halogenated aromatic compounds (e.g., chlorobenzene or dichlorobenzene); amides (e.g., hexamethylphosphoramide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine or N,N'-1,4-diformylpiperazine); nitriles (e.g., acetonitrile, propionitrile, n-butyronitrile, isobutyronitrile or benzonitrile); ketones (e.g., acetone) or mixtures thereof.

N,N-Dimethylformamide, N,N-dimethylacetamide, tetramethylene sulphone and N-methylpyrrolidone are preferred solvents in step (i).

It is also optionally possible, in step (i), for a catalyst to be present/added. All catalysts which accelerate the reaction with the 2,2-difluoro-1-chloroethane are suitable for use in the process according to the invention. Mixtures of suitable catalysts are also conceivable. Alkali metal bromides and iodides (e.g., sodium iodide, potassium iodide or potassium bromide); ammonium bromide and ammonium iodide; tetraalkylammonium bromides and iodides (e.g., tetraethylammonium iodide or tetrabutylammonium bromide); certain phosphonium halides, such as tetraalkyl- or tetraarylphosphonium halides (e.g., hexadecyltributylphosphonium bromide, stearyltributylphosphonium bromide, tetrabutylphosphonium bromide, tetraoctylphosphonium bromide, tetraphenylphosphonium chloride and tetraphenylphosphonium bromide), tetrakis(dimethylamino)phosphonium bromide, tetrakis(diethylamino)phosphonium bromide, tetrakis(dipropylamino)phosphonium chloride or tetrakis(dipropylamino)phosphonium bromide; and bis(dimethylamino)[(1,3-dimethylimidazolidin-2-ylidene)amino]methylium bromide are suitable in particular according to the invention.

Use is made in the process according to the invention, as catalyst, of preferably sodium bromide, potassium bromide, sodium iodide, potassium iodide, tetrabutylammonium bromide or tetraphenyl-phosphonium bromide and of particularly preferably tetrabutylammonium bromide, in particular tetra(n-butyl)ammonium bromide, sodium iodide or potassium iodide.

The catalyst can also be produced in situ, for example by a reaction of HBr or HI with ammonia. Furthermore, the catalyst can also be produced in situ by addition of highly reactive alkyl bromides or iodides (e.g., methyl bromide, ethyl bromide, methyl iodide or ethyl iodide).

In the process according to the invention, the catalyst is used, based on the imide of the formula (II) used, in a concentration of approximately 0.01 to approximately 25% by weight. Higher concentrations are possible in principle. The catalyst is preferably used in a concentration of approximately 0.2 to approximately 25% by weight, particularly preferably of approximately 0.4 to approximately 20% by weight and very particularly preferably of approximately 0.5 to approximately 15% by weight. However, the catalyst can also preferably be used in a concentration of approximately 0.05 to approximately 4% by weight, of approximately 0.1 to approximately 11% by weight or of approximately 0.5 to approximately 11% by weight.

The reaction of step (i) is advantageously carried out in the presence of one or more acid scavengers which are able to bind the hydrogen chloride released in the reaction, by which the yield is increased.

Organic and inorganic bases which are able to bind the hydrogen chloride released are suitable acid scavengers. Examples of organic bases are tertiary nitrogen bases, such as, e.g., tertiary amines, substituted or unsubstituted pyridines and substituted or unsubstituted quinolines, triethylamine, trimethylamine, diisopropylethylamine, tri-n-propylamine, tri-n-butylamine, tri-n-hexylamine, tricyclo-hexylamine, N-methylcyclohexylamine, N-methylpyrrolidine, N-methylpiperidine, N-ethylpiperidine, N,N-dimethylaniline, N-methylmorpholine, pyridine, 2-, 3- or 4-picoline, 2-methyl-5-ethylpyridine, 2,6-lutidine, 2,4,6-collidine, 4-dimethylaminopyridine, quinoline, quinaldine, N,N,N,N-tetramethyl-ethylenediamine, N,N-dimethyl-1,4-diazacyclohexane, N,N-diethyl-1,4-diazacyclohexane, 1,8-bis(di-methylamino)naphthalene, diazabicyclooctane (DABCO), diazabicyclononene (DBN), diazabicycloundecene (DBU), butylimidazole and methylimidazole.

Examples of inorganic bases are alkali metal or alkaline earth metal hydroxides, hydrogencarbonates or carbonates and other inorganic aqueous bases; preference is given, e.g., to sodium hydroxide, potassium hydroxide, lithium hydroxide, calcium hydroxide, sodium carbonate, potassium carbonate, sodium hydrogencarbonate, potassium hydrogencarbonate and sodium acetate. Potassium carbonate or sodium carbonate is very particularly preferred.

The molar ratio of acid scavenger, in particular of abovementioned bases, to the imide of the formula (II) used lies in the range from approximately 0.8 to approximately 5, preferably in the range from approximately 0.9 to approximately 4 and particularly preferably in the range from approximately 1 to approximately 3. The use of larger amounts of base is technically possible.

The molar ratio of 2,2-difluoro-1-chloroethane to the imide of the formula (II) used normally lies in the range from approximately 0.3 to approximately 30, preferably in the range from approximately 0.5 to approximately 10 and particularly preferably in the range from approximately 1 to approximately 8, or from approximately 1 to approximately 4, or from approximately 2 to approximately 4. The 2,2-difluoro-1-chloroethane can also be used as solvent, in which case the abovementioned ratios are correspondingly increased.

The imide of the formula (II) and the base can also be introduced into the 2,2-difluoro-1-chloroethane.

The reaction of step (i) is carried out in principle under intrinsic pressure in a pressure-resistant closed test vessel (autoclave). The pressure during the reaction (i.e., the intrinsic pressure) depends on the reaction temperature used, on the amount of 2,2-difluoro-1-chloroethane and on the solvent used, if a solvent is present in step (i). If an increase in pressure is desired, an additional increase in pressure can be achieved by adding an inert gas, such as nitrogen or argon.

The process according to the invention can be carried out continuously or batchwise. It is likewise conceivable to carry out some steps of the process according to the invention continuously and the remaining steps batchwise. Continuous steps within the meaning of the invention are those in which the inflow of compounds (starting materials) into a reactor and the outflow of compounds (products) from the reactor take place simultaneously but separately in space, while, with batchwise steps, the sequence inflow of compounds (starting materials), optionally chemical reaction, and outflow of compounds (products) take place one after another chronologically.

It is preferable, in carrying out reaction step (i), for the internal temperature to lie in the range from approximately 90° C. to approximately 160° C., particularly preferably in the range from approximately 90° C. to approximately 140° C.

The reaction time of the reaction in step (i) is short and lies in the range from approximately 0.5 to approximately 20 hours. A longer reaction time is possible but is not useful economically.

The reaction mixture from step (i) is worked up depending on the physical properties of the product. If phthalimide or a substituted phthalimide is used as compound of the formula (II), first the solvent is removed under vacuum. If succinimide is used as compound of the formula (II), then first the solids are filtered off. Following that, the "diluting" of the reaction mixture, i.e. addition of water in which salts may be dissolved, is normally carried out. The product can then be isolated by filtration or can be extracted from the aqueous phase using an organic solvent.

In step (ii), the cleaving of the imide of the formula (III) to give 2,2-difluoroethylamine or a salt thereof is carried out by the addition of acid, base or hydrazine. Preferably, an acid or hydrazine is used in step (ii).

The bases which can be used in step (ii) are known to a person skilled in the art or comprise the bases mentioned in the present case as acid scavenger. The acids used in step (ii) are organic or inorganic acids, inorganic acids being preferably used. Examples of such preferred inorganic acids according to the invention are hydrochloric acid, hydrobromic acid, sulphuric acid and phosphoric acid.

The cleaving of the imide of the formula (III) in step (ii) is carried out in a suitable solvent. Here also, the solvent is preferably used in such an amount that the reaction mixture remains stirrable during the whole of the process. Use is advantageously made, based on the imide of the formula (III) used, of the solvent in an amount of approximately 1 to 50 times (v/v), preferably in an amount of approximately 2 to 40 times and particularly preferably in an amount of 2 to 10 times.

All organic solvents which are inert under the reaction conditions are possible as solvent. The term "solvent" is also understood to mean, according to the invention, mixtures of pure solvents.

Suitable solvents according to the invention in step (ii) are in particular water, ethers (e.g., ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, 2-methyltetrahydrofuran, dioxane, and ethylene oxide and/or propylene oxide polyethers); aliphatic, cycloaliphatic or aromatic hydrocarbons (e.g., pentane, hexane, heptane, octane, nonane, such as white spirits with components with boiling points in the range, for example, from 40° C. to 250° C., cymene, benzene fractions within a boiling point interval from 70° C. to 190° C., cyclohexane, methylcyclohexane, petroleum ether, ligroin, octane, benzene, toluene or xylene); linear and branched carboxylic acids (e.g., formic acid, acetic acid, propionic acid, butyric acid and isobutyric acid) and the esters thereof (e.g., ethyl acetate and butyl acetate); alcohols (e.g., methanol, ethanol, isopropanol, n-butanol and isobutanol) or mixtures thereof. Preferred solvents according to the invention in step (ii) are methanol, ethanol and water or mixtures thereof.

The molar ratio of acid or hydrazine to imide of the formula (III) used lies in the range from approximately 0.8 to approximately 100, preferably in the range from approximately 1 to approximately 20 and particularly preferably in the range from approximately 1.1 to approximately 10. The addition of larger amounts of acid or hydrazine is possible in principle. With suitable manageability, the acid can also be used as solvent.

The cleaving in step (ii) can be carried out at temperatures in the range from approximately 0° C. to approximately 150° C. The internal temperature preferably lies in the range from approximately 20° C. to approximately 130° C.; it particularly preferably lies in the range from approximately 40° C. to 110° C.

The reaction time for the cleaving is short and lies in the range from approximately 0.1 to 12 hours. A longer reaction time is possible but is not useful economically.

After the end of the reaction, the 2,2-difluoroethylamine obtained can be purified by distillation. Alternatively, the 2,2-difluoroethylamine can also be isolated and purified as salt, e.g. hydrochloride. The 2,2-difluoroethylamine salt can subsequently be released by addition of base.

The present invention is more fully described from the following examples, without the invention by this being limited to these.

PREPARATION EXAMPLES

Example 1

Preparation of 2-(2,2-difluoroethyl)-1H-isoindole-1,3(2H)-dione (step (i))

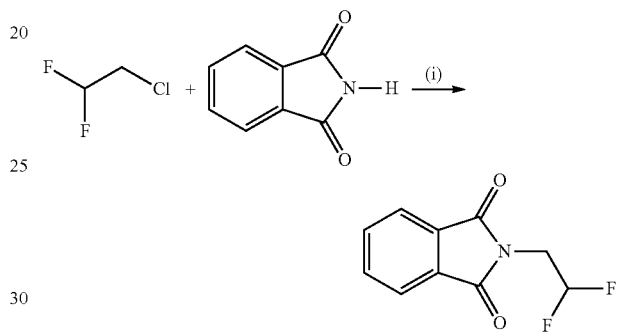

Example 1.1

An amount of 27.6 g (0.269 mol) of 2,2-difluoro-1-chloroethane, 2.16 g (6.73 mmol) of tetra(n-butyl)ammonium bromide and 20 g (0.135 mol) of phthalimide are dissolved in 95 g of N,N-dimethylformamide and treated with 46.96 g (0.336 mol) of potassium carbonate. The reaction mixture is stirred in an autoclave under pressure at 120° C. for 16 h. After the end of the reaction, cooling is carried out to ambient temperature and the solvent is exhaustively removed under vacuum. The remaining residue is treated with 150 ml of water and the solid is filtered off. The filter residue is washed twice with water and the product is dried under vacuum. An amount of 28.5 g of 2-(2,2-difluoroethyl)-1H-isoindole-1,3 (2H)-dione with a purity of 97.4% is obtained. This corresponds to a yield of 97.7% of theory.

$^1$H NMR (CDCl$_3$): 7.91 (d, 2H), 7.7 (d, 2H), 6.06 (tt, 1H), 4.07 (dt, 2H).

Example 1.2

An amount of 27.6 g (0.269 mol) of 2,2-difluoro-1-chlorethane, 2.16 g (6.73 mmol) of tetra(n-butyl)ammonium bromide and 20 g (0.135 mol) of phthalimide are dissolved in 95 g of N,N-dimethylformamide and treated with 28.18 g (0.201 mol) of potassium carbonate. The reaction mixture is stirred in an autoclave under pressure at 120° C. for 16 h. After the end of the reaction, cooling is carried out to ambient temperature and the solvent is exhaustively removed under vacuum.

The remaining residue is treated with 100 ml of water and the solid is filtered off. The filter residue is washed twice with water and the product is dried under vacuum. An amount of 24.9 g of 2-(2,2-difluoroethyl)-1H-isoindole-1,3(2H)-dione with a purity of 99.5% is obtained. This corresponds to a yield of 87.2% of theory.

$^1$H NMR (CDCl$_3$): 7.91 (d, 2H), 7.7 (d, 2H), 6.06 (tt, 1H), 4.07 (dt, 2H).

Example 1.3

Comparative Example

An amount of 21.4 g (0.214 mol) of 2,2-difluoro-1-chloroethane and 20 g (0.107 mol) of potassium phthalimide are dissolved in 95 g of N,N-dimethylformamide. The reaction mixture is stirred in an autoclave under pressure at 120° C. for 12 h. After the end of the reaction, cooling is carried out to ambient temperature and the solvent is exhaustively removed under vacuum. The remaining residue is treated with 100 ml of water and the solid is filtered off. The filter residue is washed twice with water and the product is dried under vacuum. An amount of 22.5 g of 2-(2,2-difluoroethyl)-1H-isoindole-1,3(2H)-dione with a purity of only 59% is obtained. This corresponds to a yield of 59% of theory.

$^1$H NMR (CDCl$_3$): 7.91 (d, 2H), 7.7 (d, 2H), 6.06 (tt, 1H), 4.07 (dt, 2H).

Example 1.4

An amount of 54.25 g (0.529 mol) of 2,2-difluoro-1-chloroethane, 9.1 g (0.066 mol) of potassium carbonate and 50 g (0.264 mol) of potassium phthalimide are dissolved in 237 g of N,N-dimethylformamide. The reaction mixture is stirred in an autoclave under pressure at 120° C. for 12 h. After the end of the reaction, cooling is carried out to ambient temperature and the solvent is exhaustively removed under vacuum. The remaining residue is treated with 250 ml of water and the solid is filtered off. The filter residue is washed twice with water and the product is dried under vacuum. An amount of 55.5 g of 2-(2,2-difluoroethyl)-1H-isoindole-1,3(2H)-dione with a purity of 96.5% is obtained. This corresponds to a yield of 95.8% of theory.

$^1$H NMR (CDCl$_3$): 7.91 (d, 2H), 7.7 (d, 2H), 6.06 (tt, 1H), 4.07 (dt, 2H).

Example 1.5

An amount of 27.6 g (0.269 mol) of 2,2-difluoro-1-chloroethane and 20 g (0.135 mol) of phthalimide are dissolved in 95 g of N,N-dimethylformamide and treated with 56.3 g (0.403 mol) of potassium carbonate. The reaction mixture is stirred in an autoclave under pressure at 120° C. for 16 h. After the end of the reaction, cooling is carried out to ambient temperature and the solvent is exhaustively removed under vacuum. The remaining residue is treated with 100 ml of water and the solid is filtered off. The filter residue is washed twice with water and the product is dried under vacuum. An amount of 22.2 g of 2-(2,2-difluoroethyl)-1H-isoindole-1,3 (2H)-dione with a purity of 98.4% is obtained. This corresponds to a yield of 77% of theory.

$^1$H NMR (CDCl$_3$): 7.91 (d, 2H), 7.7 (d, 2H), 6.06 (tt, 1H), 4.07 (dt, 2H).

Example 2

Preparation of 1-(2,2-difluoroethyl)pyrrolidine-2,5-dione (step (i))

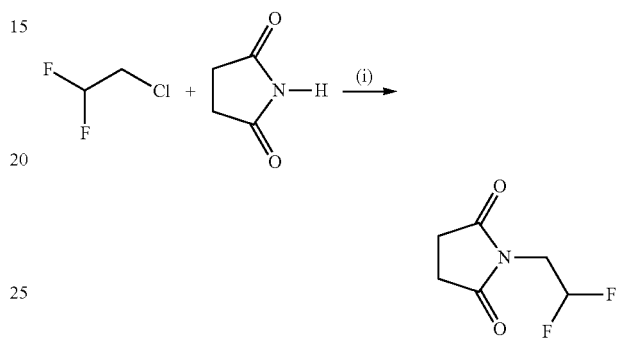

Example 2.1

An amount of 204.9 g (1.9 mol) of 2,2-difluoro-1-chloroethane, 3.22 g (9.9 mmol) of tetra(n-butyl)ammonium bromide and 20 g (0.19 mol) of succinimide are treated with 83.6 g (0.599 mol) of potassium carbonate. The reaction mixture is stirred in an autoclave under pressure at 120° C. for 16 h. After the end of the reaction, cooling is carried out to ambient temperature and the reaction mixture is subsequently filtered. The filter residue is washed with dichloromethane and the solvent is removed under vacuum. An amount of 36.5 g of 1-(2,2-difluoroethyl)pyrrolidine-2,5-dione with a purity of 85% is obtained. This corresponds to a yield of 95% of theory.

$^1$H NMR (CDCl$_3$): 5.99 (tt, 1H), 3.89 (dt, 2H), 2.79 (s, 4H),
$^{19}$F NMR: −123.15 (dt, CF$_2$H).

Example 2.2

An amount of 40.9 g (0.39 mol) of 2,2-difluoro-1-chloroethane, 3.22 g (9.9 mmol) of tetra(n-butyl)ammonium bromide, 95 g of N,N-dimethylformamide and 20 g (0.19 mol) of succinimide are treated with 83.6 g (0.599 mol) of potassium carbonate. The reaction mixture is stirred in an autoclave under pressure at 120° C. for 16 h. After the end of the reaction, cooling is carried out to ambient temperature and the reaction mixture is subsequently filtered. The filter residue is washed with dichloromethane and the solvent is removed under vacuum. The oil is once more treated with 30 ml of water and extracted twice with 30 ml of dichloromethane. The combined organic phases are dried and the solvent is removed under vacuum. An amount of 27.3 g of 1-(2,2-difluoroethyl)pyrrolidine-2,5-dione with a purity of 93% is obtained. This corresponds to a yield of 77.8% of theory.

$^1$H NMR (CDCl$_3$): 5.99 (tt, 1H), 3.89 (dt, 2H), 2.79 (s, 4H).

Example 3

Preparation of 2,2-difluoroethylamine (step (ii))

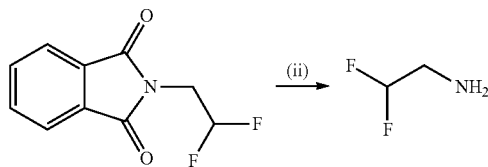 [SMILES: O=C1c2ccccc2C(=O)N1CC(F)F ; NCC(F)F]

Example 3.1

An amount of 10 g (0.046 mol) of 2-(2,2-difluoroethyl)-1H-isoindole-1,3(2H)-dione in 50 ml of ethanol in a reaction flask is treated with 3.16 g (0.063 mol) of hydrazine hydrate. The reaction mixture is heated to reflux and stirred at reflux for 16 h. Cooling is carried out to 50° C. and the reaction mixture is adjusted to pH 2 with 6 ml of 32% hydrochloric acid. It is again briefly heated to reflux and subsequently cooled to ambient temperature, and the solid is filtered off. The mother liquor is concentrated to dryness. The 3.9 g of 2,2-difluoroethylamine are obtained as hydrochloride (corresponds to 71.4% of theory).

$^1$H NMR (D$_2$O): 6.31 (tt, 1H), 3.51 (dt, 2H).

Example 3.2

An amount of 10 g (0.046 mol) of 2-(2,2-difluoroethyl)-1H-isoindole-1,3(2H)-dione in 50 ml of water in a reaction flask is treated with 50 ml of 32% hydrochloric acid. The reaction mixture is heated to reflux and stirred at reflux for 20 h. Subsequently, the reaction mixture is cooled to ambient temperature and the solid is filtered off. The mother liquor is concentrated to dryness. The 5.2 g of 2,2-difluoroethylamine are obtained as hydrochloride with a content of 93% (corresponds to 88% of theory).

$^1$H NMR (D$_2$O): 6.31 (tt, 1H), 3.51 (dt, 2H).

Example 4

Preparation of 2,2-difluoroethylamine (step (ii))

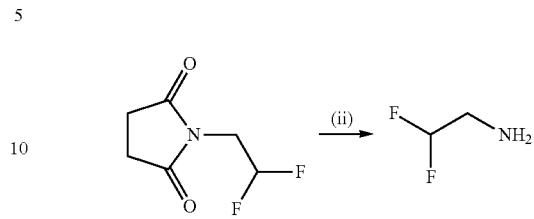

Example 4.1

An amount of 10 g (0.052 mol) of 1-(2,2-difluoroethyl) pyrrolidine-2,5-dione in 50 ml of water in a reaction flask is treated with 50 ml of 32% hydrochloric acid. The reaction mixture is heated to reflux, stirred at reflux for 22 h and subsequently cooled to ambient temperature, and the solid is filtered off. The mother liquor is concentrated to dryness. The 3.1 g of 2,2-difluoroethylamine are obtained as hydrochloride (corresponds to 50% of theory).

$^1$H NMR (D$_2$O): 6.31 (tt, 1H), 3.51 (dt, 2H).

The invention claimed is:

1. A compound of formula (III-a)

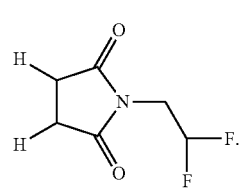

(III-a)

* * * * *